US011091723B2

(12) United States Patent
Betzer et al.

(10) Patent No.: US 11,091,723 B2
(45) Date of Patent: Aug. 17, 2021

(54) USE OF AMBROCENIDE® FOR INTENSIFYING A LILY OF THE VALLEY SCENT

(71) Applicant: SYMRISE AG, Holzminden (DE)

(72) Inventors: Marcus Betzer, Holzminden (DE); Stefan Lambrecht, Hehlen (DE); Marcus Eh, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/636,710

(22) PCT Filed: Aug. 9, 2017

(86) PCT No.: PCT/EP2017/070219
§ 371 (c)(1),
(2) Date: Feb. 5, 2020

(87) PCT Pub. No.: WO2017/174827
PCT Pub. Date: Oct. 12, 2017

(65) Prior Publication Data
US 2020/0239810 A1   Jul. 30, 2020

(51) Int. Cl.
C11D 3/50 (2006.01)
C11B 9/00 (2006.01)
A61K 8/49 (2006.01)
A61Q 5/02 (2006.01)
A61Q 19/10 (2006.01)

(52) U.S. Cl.
CPC ............ *C11B 9/0076* (2013.01); *A61K 8/498* (2013.01); *A61K 8/4973* (2013.01); *A61Q 5/02* (2013.01); *A61Q 19/10* (2013.01); *C11B 9/008* (2013.01)

(58) Field of Classification Search
CPC ...... A61K 8/342; A61K 8/4973; A61K 8/498; C11D 3/50; C11D 3/505; C11B 9/0076; C11B 9/008; C07C 31/1355; C07C 2601/14; C07D 307/12
See application file for complete search history.

(56) References Cited

U.S. PATENT DOCUMENTS

| 8,754,028 B2 | 6/2014 | Clare et al. |
| 10,526,563 B2 | 1/2020 | Schatkowski et al. |

| 2013/0230476 A1* | 9/2013 | Pelzer | C11B 9/008 424/70.1 |
| 2016/0090548 A1* | 3/2016 | Holscher | C11B 9/0088 510/103 |
| 2017/0114299 A1* | 4/2017 | Schatkowski | C11B 9/0076 |

FOREIGN PATENT DOCUMENTS

| EP | 0857723 A1 | 8/1998 | |
| EP | 2803666 A1 * | 11/2014 | ............ A61Q 19/10 |
| EP | 2947078 A1 * | 11/2015 | ........... C11B 9/0076 |
| JP | H10218877 A | 8/1998 | |
| JP | 2007154069 A | 6/2007 | |
| JP | 2017517509 A | 6/2017 | |
| WO | 2011147919 A1 | 12/2011 | |
| WO | 2012062771 A1 | 5/2012 | |
| WO | 2014180945 A1 | 11/2014 | |
| WO | 2015176833 A1 | 11/2015 | |

OTHER PUBLICATIONS

International Search Report and Written Opinion dated Sep. 20, 2017 for corresponding PCT Application No. PCT/EP2017/070219.
Anonymous: "floral pyranol", The Good Scents Company, 2017 XP055404864.
Japanese Office Action dated May 26, 2021 for corresponding Japanese Patent Application No. 2020-506821.

* cited by examiner

*Primary Examiner* — John R Hardee
(74) *Attorney, Agent, or Firm* — Polsinelli PC

(57) ABSTRACT

The present invention primarily relates to the use of one or more stereoisomers of the compound of formula (I) as described herein for modifying and/or enhancing the olfactory impression of one or more fragrances with a lily of the valley scent. The invention further relates to a new mixture comprising or consisting of one or more stereoisomers of the compound of formula (I) as described herein and two or more stereoisomers of the compound of formula (II) as described herein with a weight ratio of the stereoisomers of the compounds of formula (II) as described herein, fragrance compositions comprising or consisting of a mixture as described herein, perfumed products containing mixtures or fragrance composition as described herein, and a process for modifying and/or enhancing the lily of the valley scent of a compound of formula (II) as described herein, respectively for preparing a perfumed product as described herein.

20 Claims, No Drawings

USE OF AMBROCENIDE® FOR INTENSIFYING A LILY OF THE VALLEY SCENT

CROSS-REFERENCE TO RELATED APPLICATIONS

This application is a national stage application (under 35 U.S.C. § 371) of PCT/EP2017/070219, filed Aug. 9, 2017, which is incorporated herein by reference in its entirety.

The present invention primarily relates to the use of one or more stereoisomer(s) of the compound of formula (I) as described herein for modifying and/or enhancing the olfactory impression of one or more fragrance(s) with a lily of the valley scent. The invention further relates to a new mixture comprising or consisting of one or more stereoisomer(s) of the compound of formula (I) as described herein and two or more stereoisomers of the compound of formula (II) as described herein with a weight ratio of the stereoisomers of the compounds of formula (II) as described herein, fragrance compositions comprising or consisting of a mixture as described herein, perfumed products containing mixtures or fragrance composition as described herein, and a process for modifying and/or enhancing the lily of the valley scent of a compound of formula (II) as described herein, respectively for manufacturing a perfumed product as described herein.

Further aspects and preferred forms of the present invention result from the following explanations, the attached examples and in particular the attached patent claims.

Despite a large number of existing fragrances, the perfume industry still has a general need for new fragrances and fragrance compositions. For example, there is a need for fragrances that are capable (in fragrance compositions) of creating, besides a primary odour, further interesting notes and of expanding the possibilities of the perfumer with their novel or arbitrary olfactory properties. In particular, there is an interest in fragrances with scents that are able to combine harmoniously with floral and/or fruity fragrances. Preferably, the different olfactory aspects and notes should be superimposed in order to create an overall complex olfactory impression.

For the creation of novel compositions, there is a constant need for fragrances with special sensory properties that can serve as a basis for the composition of novel perfumes with complex sensory character.

The primary object was now to find fragrances with an interesting, preferably complex, witty sensory profile that could be used as fragrances in perfumery, for example. Within the context of this invention, compounds were explored that could modify and/or enhance a lily of the valley scent.

The searched compounds should enable the production of novel fragrance compositions with special olfactory notes and aspects. Advantageous would be those substances, which are especially suitable for combination with other fragrances which have the note "lily of the valley".

In addition, the fragrances fulfilling this primary object should preferably have additional positive secondary properties in addition to their primary, namely olfactory, properties such as high stability under certain application conditions, high extensiveness, good adhesion, high substantivity or scent-enhancing properties (so-called booster or enhancer effect) and/or, in combination with other fragrances, round off their naturalness, freshness, fullness, (radiant) power and/or radiance so that remarkable sensory effects can be achieved.

According to the invention, the primary task is solved by the use of one or more stereoisomer(s) of the compound of formula (I)

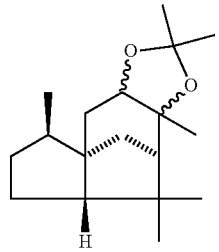

(I)

for modifying and/or enhancing, preferably for strengthening, the olfactory impression of one or more fragrance(s) with a lily of the valley scent.

In the context of the study on which this invention is based, it has surprisingly been found that the compound of formula (I) (Ambrocenide®, CAS No.: 211299-54-6) is excellently suited for modifying and/or enhancing, especially enhancing, the lily of the valley scent of various lily of the valley fragrances.

According to the present invention, one, two, three or all of the following diastereomers (Ia) to (Id) can be used as a compound of formula (I), that means the individual diastereomers (Ia) to (Id) or any mixture of these diastereomers can be used.

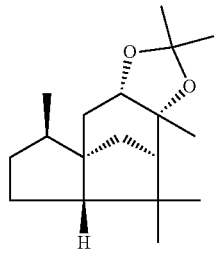

(Ia)

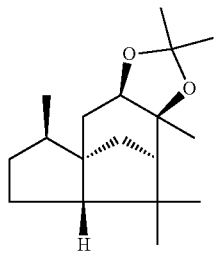

(Ib)

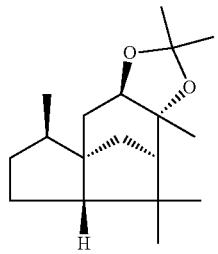

(Ic)

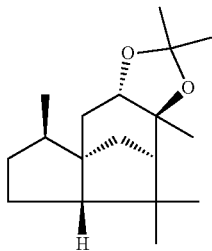

What is said herein for a compound of formula (I), especially the advantages described herein, also applies to the individual diastereomers (Ia) to (Id) and any mixture of these diastereomers (see above).

Preferably, the use according to the invention relates to a use as described herein, wherein the, one or more fragrance(s) is/are selected from the group consisting of 2-methyl-3-(4-tert.-butylphenyl)propanal, 2-methyl-3-(3-tert.-butylphenyl)propanal, 2,5,7,7-tetramethyloctanal, 4-(1,1-dimethylethyl)phenylpropanal, 3-(4-isopropylphenyl)propanal, octahydro-8,8-dimethylnaphthalene-2-carboxaldehyde, octahydro-4,7-methanoindanilydenebutanal, beta-methyl-3-(1-methylethyl)phenylpropanal, 2-methyl-3-(3,4-methylenedioxyphenyl)propanal, 7-hydroxy-3,7-dimethyloctanal, 4-(4-hydroxy-4-methylpentyl)-3-cyclohexene-1-carboxaldehyde, 2,2-dimethyl-3-(3-methylphenyl)propanol, cis-4-(1-methylethyl)cyclohexanemethanol, 1-(4-isopropylcyclohexyl)ethanol, 3-methyl-4-phenylbutan-2-ol, dimethylphenyl-propanol, 2-methyl-3-(4-(2-methylpropyl)phenyl)propanal, 3-(4-isobutylphenyl)-2-methylpropanal, 3,4-Dioxy(cycloacetonyl)toluene, 3-(1-ethoxyethoxy)-3,7-dimethyl-1,6-octadiene, alpha,alpha-dimethyl-4-ethylphenyl-propanal, gamma-methylphenylpentanal and compound of formula (II),

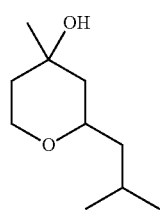
(II)

preferably wherein the fragrance is a compound of formula (II).

Especially preferred is the use as described herein, wherein the fragrance(s) comprise or consist of one or more stereoisomer(s) of the compound of formula (II)

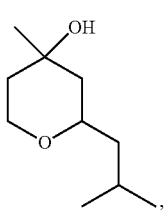
(II)

wherein preferably the weight ratio of the total amount of compounds of the formula cis-(II)(+) and cis-(II)(−)

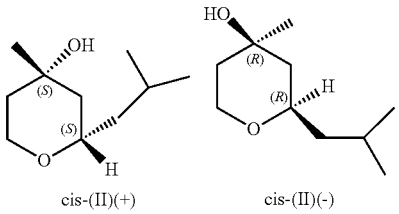

cis-(II)(+)      cis-(II)(−)

to the total amount of compounds of the formula trans-(II)(+) and trans-(II)(−)

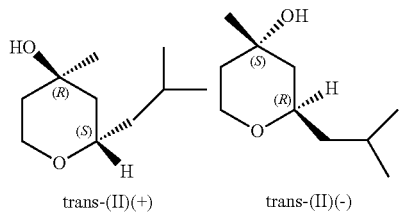

trans-(II)(+)      trans-(II)(−)

is between 65:35 and 95:5, preferably 70:30 and 90:10, especially preferred between 75:25 and 85:15.

The use according to the invention of the compound of formula (II) as described herein with an isomer ratio in the range defined above is especially preferred in the context of the present invention. The compound of formula (II) as described herein with an isomer ratio in the range defined above is known, for example, under the trade name pyranol. Pyranol is relatively volatile and has a soft floral fragrance with a typical note of lily of the valley (muguet) which, according to the present invention, surprisingly appears more natural and radiant by the addition of one or more stereoisomers of the compound of formula (I). In addition, the addition of one or more stereoisomers of the compound of formula (I) makes the lily of the valley scent of pyranol more noticeably (boost effect) and increases its substantivity.

Some isomer mixtures of the compound of formula (II), for example Florol®/Florosa®, are perceived as too expensive in some cases. Other mixtures of isomers, e.g. pyranol, are partly perceived as olfactory substances with less character, less radiation and/or less adhesion of the fragrance in relation to other mixtures of isomers of the compound of formula (II) with respect to its olfactory properties. Surprisingly, the addition of one or more stereoisomers of the compound of formula (I) leads to a sensory enhancement (see examples below), i.e. to more character, more radiation and/or more adhesion of the fragrance.

Another advantage of using compounds of the formula (II) over other fragrances with a lily of the valley scent (as listed above) is that the compounds of the formula (II) are less subject to regulatory burden (harmless classification/labelling) and have a better cost/performance ratio.

According to one embodiment of the use according to the invention, it is preferred if the total amount of compounds of the formula cis-(II)(+) and cis-(II)(−) comprises predominantly—that means more than 50% by weight relative to the total amount of compounds of the formula cis-(II)(+) and cis-(II)(−)—of the compound of the formula cis-(II)(−), preferably if it comprises 60, 70, 80 or 90% by weight of the compounds of the formula cis-(II)(+) and cis-(II)(−), or if it consists essentially, preferably 100% by weight relative to the total amount of compounds of formula cis-(II)(+) and cis-(II)(−), of compound of formula cis-(II)(−).

According to one embodiment of the use according to the invention, it is preferred when the total amount of compounds of formula cis-(II)(+) and cis-(II)(−) comprises predominantly, that means more than 50% by weight relative to the total amount of compounds of formula cis-(II)(+) and cis-(II)(−), of compound of formula cis-(II)(+), preferably when it comprises 60, 70, 80 or 90% by weight of a compound of formula cis-(II)(+) and cis-(II)(−), or if it consists essentially, preferably 100% by weight relative to the total amount of compounds of formula cis-(II)(+) and cis-(II)(−), of compound of formula cis-(II)(+).

According to another aspect, the present invention also relates to a mixture comprising or consisting of one or more stereoisomer(s) of the compound of formula (I)

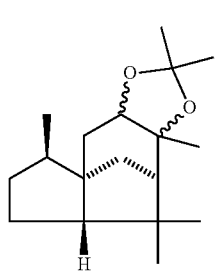
(I)

and two or more stereoisomers of the compound of formula (II),

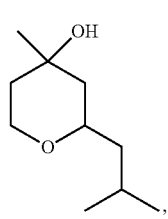
(II)

wherein the weight ratio of the total amount of compounds of the formula cis-(II)(+) and cis-(II)(−)

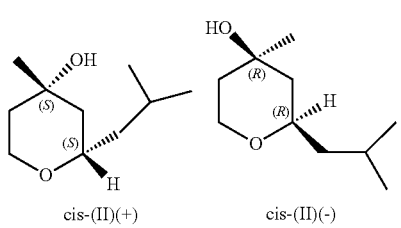
cis-(II)(+)    cis-(II)(−)

to the total amount of compounds of the formula trans-(II)(+) and trans-(II)(−)

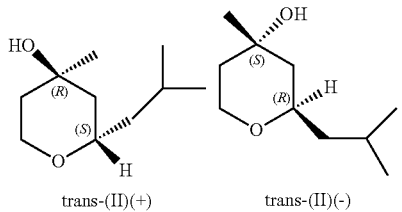
trans-(II)(+)    trans-(II)(−)

is between 65:35 and 95:5, preferably 70:30 and 90:10, especially preferred between 75:25 and 85:15.

Preferred is a mixture as described herein, wherein the weight ratio of the total amount of stereoisomer(s) of the compound of the formula (I)

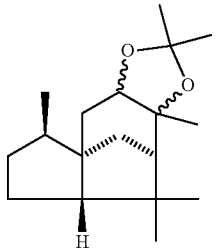
(I)

to the total amount of stereoisomers of the compound of formula (II)

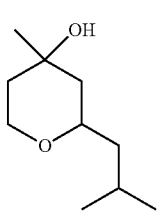
(II)

is between 1:12000 and 1:0.5, preferably between 1:600 and 1:0.7, especially preferably between 1:100 and 1:1, and/or wherein the total amount of stereoisomer(s) of the compound of formula (I) is sufficient to modify and/or enhance, preferably enhance, the olfactory impression of the two or more stereoisomers of the compound of formula (II).

According to another aspect, the present invention also relates to a method for modifying and/or enhancing, preferably enhancing, the lily of the valley scent of a compound of formula (II) comprising or consisting of the following steps:

i) Providing one or more stereoisomer(s) of the compound of formula (I)

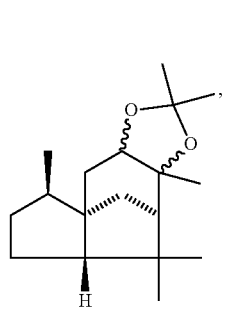
(I)

ii) Providing two or more stereoisomers of the compound of formula (II)

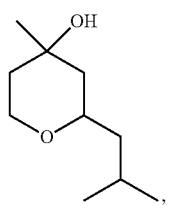
(II)

wherein the weight ratio of the total amount of compounds of the formula cis-(II)(+) and cis-(II)(−)

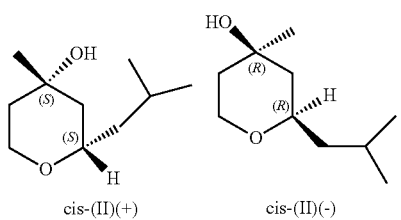

cis-(II)(+)   cis-(II)(-)

to the total amount of compounds of the formula trans-(II)(+) and trans-(II)(−)

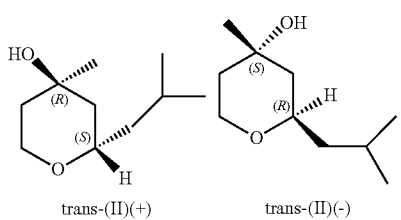

trans-(II)(+)   trans-(II)(-)

is between 65:35 and 95:5, preferably 70:30 and 90:10, especially preferred 75:25 and 85:15, iii) Mixing the compounds provided in steps i) and ii), preferably wherein the amount of the one or more stereoisomer(s) of the compound of formula (I) is sufficient to modify and/or enhance, preferably enhance, the lily of the valley scent of the compound of formula (II).

Preferred is a method according to the invention as described herein, wherein the weight ratio of the total amount of stereoisomer(s) of the compound of formula (I)

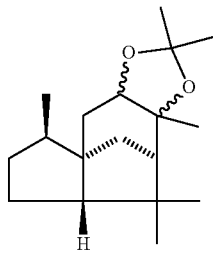
(I)

to the total amount of stereoisomers of the compound of formula (II)

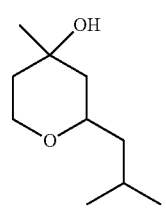
(II)

is between 1:12000 and 1:0.5, preferably between 1:600 and 1:0.7, especially preferred between 1:10 and 1:1.

Another aspect of the present invention relates to a mixture, preferably a mixture as described herein, obtainable by a method comprising or consisting of the following steps:

i) Providing one or more stereoisomers of the compound of formula (I)

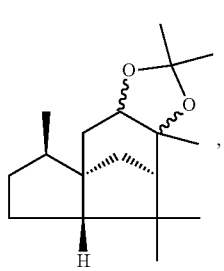
(I)

ii) Providing two or more stereoisomers of the compound of formula (II),

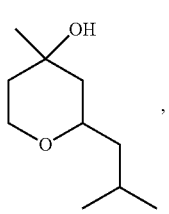
(II)

wherein the weight ratio of the total amount of compounds of the formula cis-(II)(+) and cis-(II)(−)

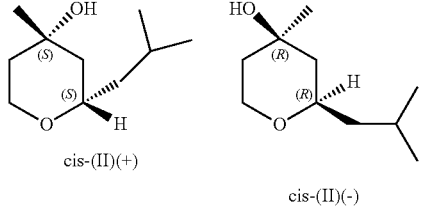

cis-(II)(+)          cis-(II)(−)

to the total amount of compounds of the formula trans-(II)(+) and trans-(II)(−)

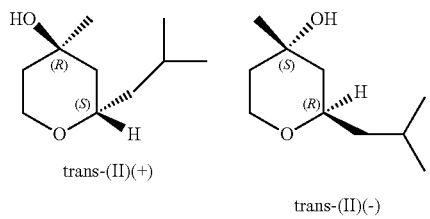

trans-(II)(+)          trans-(II)(−)

is between 65:35 and 95:5, preferably 70:30 and 90:10, especially preferred 75:25 and 85:15,
(iii) Mixing the compounds provided in steps (i) and (ii).

According to another aspect, the present invention also relates to a fragrance composition, preferably perfume oil, comprising or consisting of a mixture as described herein, and preferably further of one or more additional fragrances, preferably wherein the additional or one, more or all of the additional fragrances is selected or are selected from the group consisting of 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-Trimethyl-1-cyclohex-2-enyl)but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]-but-3-en-2-one, 1-(2,6,6-Trimethyl-1-cyclohex-2-enyl)pent-1-en-3-one, [(Z)-Hex-3-enyl] methyl carbonate, 3-[(Z)-Hex-3-enoxy] propannitrile, 1-(2,3,8,8-tetramethyl-1,3,4,5,6,7-hexahydronaphthalen-2-yl)ethanone, spiro[1,3-dioxolane-2,5′-(4′,4′,8′,8′-tetramethyl-hexahydro-3′,9′-methanonaphthalene)],[3R-(3α,3aβ,6β,7β,8aα)]-octahydro-6-methoxy-3,6,8,8-tetramethyl-1H-3a,7-methanoazulen, [3R-(3α,3aβ,7β,8aα)]-1-(2,3,4,7,8,8a-hexahydro-3,6,8,8-tetramethyl-1H-3a,7-methano-azulen-5-yl)ethan-1-one, 1-(2,2,6-trimethyl-cyclohexyl) hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethyl-octa-1,6-dien-3-yl)acetate, (4-methyl-1-propan-2-yl-1-cyclohex-2-enyl)acetate, (8E)-cyclohexadec-8-en-1-one, 1,3,4,6,7,8-hexahydro-4,6,6,7,8,8-hexamethyl-cyclopenta(g)-2-benzopyran, ethoxymethoxy-cyclododecane, 1,1,2,3,3-pentamethyl-2,5,6,7-tetrahydroinden-4-one, 1-(2,3,8,8-tetramethyl-1,3,4,5,6,7-hexa-hydronaphthalen-2-yl) ethanone.

Preferred is a fragrance composition as described herein, wherein the total amount of stereoisomer(s) of the compound of formula (I)

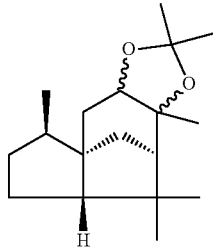

(I)

is sufficient to modify and/or enhance, preferably enhance the olfactory impression of the two or more stereoisomers of the compound of formula (II).

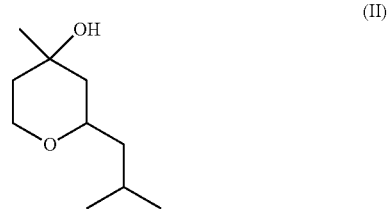

(II)

Further preferred is a fragrance composition according to the invention as described herein, preferably a perfume oil, wherein the total amount of stereoisomer(s) of the compound of formula (I)

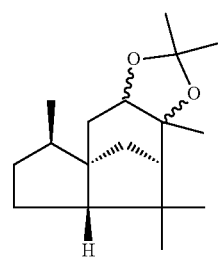

(I)

is 0.0001 to 10% by weight, preferably 0.001 to 5% by weight, especially preferred 0.01 to 1% by weight, based on the total weight of the fragrance composition.

A further aspect of the present invention relates to a perfumed product, comprising a mixture according to the invention as described herein, or preferably a fragrance composition according to the invention as described herein, preferably a perfume oil, in a sensory effective amount, wherein the amount of the mixture or fragrance composition, based on the total weight of the product, is preferably in the range of 0.01 to 100% by weight, preferably 0.02 to 50% by weight, especially preferred 0.1 to 20% by weight, preferably wherein the product is selected from the group consisting of perfume extraits, eau de parfums, eau de toilettes, shaving lotions, eau de colognes, pre-shave products, splash colognes, perfumed refreshing tissues, acidic, alkaline and neutral detergents, textile fresheners, ironing aids, liquid detergents, powdery detergents, laundry pre-treatments, fabric softeners, laundry soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

Another aspect of the present invention relates to a method for manufacturing a perfumed product, preferably a product according to the invention as described herein, comprising the following steps:

i) Providing a mixture according the invention as described herein or a fragrance composition according the invention as described herein, (ii) Providing one or more other components of the perfumed product to be manufactured; and (iii) Contacting or mixing the other components provided in step (ii) with a sensory effective amount of the ingredients provided in step (i).

For the aspects according to the invention as described above, what has been said above in connection with a use according to the invention shall preferably apply mutatis mutandis to the aspects according to the invention as described above, and likewise what has been said in connection with the aspects according to the invention as described above shall apply mutatis mutandis to the use according to the invention. Furthermore, the embodiments as described herein can be combined arbitrarily with each other, as far as it is technically reasonable.

This invention is explained in more detail using the following examples. Unless otherwise stated, all specifications refer to the weight.

EXAMPLES

Preferred Mixtures of Pyranol and Ambrocenide®

Mixture 1

| PYRANOL | 1,000.00 |
| AMBROCENIDE ® | 0.1 |

Effect: The lily of the valley scent of the pyranol is enhanced and more concise, which goes along with a higher value.

Mixture 2

| PYRANOL | 1,000.00 |
| AMBROCENIDE ® | 1 |

Effect: The lily of the valley scent of pyranol becomes more substantive and natural, making the mixture 2 appear more valuable.

Perfume Oils 1

|  | A | B | C | D |
|---|---|---|---|---|
| ALDEHYD C14 SOG | 3.00 | 3 | 3 | 3 |
| AMBROXIDE | 15 | 15 | 15 | 15 |
| BENZOE SIAM ABS. | 30 | 30 | 30 | 30 |
| BENZYLACETAT FG | 2 | 2 | 2 | 2 |
| BHT JONOL | 2 | 2 | 2 | 2 |
| CASHMERAN | 20 | 20 | 20 | 20 |
| CUMARIN | 7 | 7 | 7 | 7 |
| DECALACTON GAMMA | 4 | 4 | 4 | 4 |
| DIPROPYLENGLYCOL | 69.5 | 69.5 | 69.5 | 69.5 |
| EBANOL | 15 | 15 | 15 | 15 |
| ETHYLENBRASSYLATE | 150 | 150 | 150 | 150 |
| ETHYLMALTOL | 10 | 10 | 10 | 10 |
| FLOROSA | 120 |  |  |  |
| PYRANOL |  | 120 |  |  |
| HEXENOL CIS-3 10% DPG | 8 | 8 | 8 | 8 |
| HEXENYLACETATE CIS-3 | 1 | 1 | 1 | 1 |
| INDOL FF 1% DPG | 5 | 5 | 5 | 5 |
| ISO E SUPER | 320 | 320 | 320 | 320 |
| ISOEUGENOL 10% DPG | 1.5 | 1.5 | 1.5 | 1.5 |
| JASMIN ABS. SAMBAC REF.A 50% BB | 1.5 | 1.5 | 1.5 | 1.5 |
| JASMON CIS | 1 | 1 | 1 | 1 |
| METHYLANTHRANILATE 10% DPG | 0.5 | 0.5 | 0.5 | 0.5 |
| MUSCENONE | 7 | 7 | 7 | 7 |
| MUSCONE | 7 | 7 | 7 | 7 |
| NORLIMBANOL | 15 | 15 | 15 | 15 |
| POLYSANTOL (MYSANTOL) | 30 | 30 | 30 | 30 |
| RED BERRIES EXTRACT | 5 | 5 | 5 | 5 |
| SANDRANOL ® | 150 | 150 | 150 | 150 |
| Mixture 1 |  |  | 120 |  |
| Mixture 2 |  |  |  | 120 |
| TOTAL | 1000 | 1000 | 1000 | 1000 |

Perfume oil A: Standard fragrance composition with Florosa® as lily of the valley fragrance Perfume oil B: Florosa® from perfume oil A is replaced by pyranol. The fragrance of perfume oil B is less floral, less radiant and loses complexity compared to perfume oil A. The fragrance of perfume oil A is less floral, less radiant and less complex.

Perfume oil C: Florosa® from perfume oil A is replaced by mixture 1 (as described above). Perfume oil C's fragrance is more radiant than perfume oil B, has more body and better hedonics.

Perfume oil D: Florosa® from perfume oil A is replaced by mixture 2 (as described above). The fragrance of perfume oil D is stronger and more substantive compared to perfume oil B. In addition, perfume oil D is also more radiant and complex, and overall more performant than perfume oil A.

Perfume Oils 2

|  | E | F | G |
|---|---|---|---|
| AMAROCIT® | 10 | 10 | 10 |
| AMBRETTOLIDE | 1.5 | 1.5 | 1.5 |
| AMBROXIDE | 0.5 | 0.5 | 0.5 |
| AMYRISOEL | 2.5 | 2.5 | 2.5 |
| AURELIONE® | 25 | 25 | 25 |
| BENZYLSALICYLATE | 9 | 9 | 9 |
| BERGAMOT OIL BERGAPTEN FREE | 40 | 40 | 40 |
| CITRAL FF | 1.5 | 1.5 | 1.5 |
| CITRONELLOL L | 1.5 | 1.5 | 1.5 |
| CLARITONE® | 5 | 5 | 5 |
| DIMETHYLBENZYLCARBINYLBUTYRATE 10% DPG | 1 | 1 | 1 |
| ETHYLENBRASSYLATE | 50 | 50 | 50 |
| FLOROPAL 10% DPG | 3 | 3 | 3 |
| FLOROSA | 90 |  |  |
| GLOBALIDE® | 50 | 50 | 50 |
| HEDION HC/30 | 400 | 400 | 400 |
| HELIOTROPIN/PIPERONAL | 20 | 20 | 20 |
| HEXYLCINNAMICALDEHYDE ALPHA 10% DPG | 1 | 1 | 1 |
| ISO E SUPER | 200 | 200 | 200 |
| ISOBORNYLCYCLOHEXANOL | 10 | 10 | 10 |
| ISORALDEIN 95 | 30 | 30 | 30 |
| LINALOOL | 12 | 12 | 12 |
| MAGNOLAN | 23 | 23 | 23 |
| MANDARIN OIL | 6 | 6 | 6 |
| SANDALWOOD OIL AUSTRALIA PURE | 7.5 | 7.5 | 7.5 |
| Mixture 1 |  | 90 |  |
| Mixture 2 |  |  | 90 |
| TOTAL | 1000 | 1000 | 1000 |

Perfume oil E: Standard fragrance composition with Florosa® as lily of the valley fragrance Perfume oil F: Florosa® is replaced by mixture 1 (as described above); the olfactory improvement of the fragrance is low, but by replacing Florosa® with mixture 1, raw material costs can be saved.

Perfume oil G: Florosa® is replaced by mixture 2 (as described above); the fragrance of fragrance composition G is stronger, more substantive and has more floral character than that of Compositions E and F.

Perfumed Products

Washing Powder

| AGRUMEX LC | 150 |
|---|---|
| AMBERWOOD® F | 12 |
| BENZYLACETON | 50 |
| CITRONELLOL 950 | 2 |
| CITRONITRIL | 2 |
| CYCLAMENALDEHYDE | 1 |
| DIHYDROMYRCENOL | 200 |
| DIPROPYLENGLYCOL | 3 |
| GERANIOL SUPRA | 1 |
| HERBYLPROPIONATE | 80 |
| HEXYLACETATE | 45 |
| IONON ALPHA | 2 |
| IONON BETA | 6 |
| ISO E SUPER | 250 |
| ISODAMASCON® | 1 |
| LINALOOL | 20 |
| MACROLIDE® SUPRA | 10 |
| MAGNOLAN | 2 |
| MANZANATE | 1 |
| NEROLIONE 10% DPG | 2 |
| ORANGE OIL | 15 |
| PHENIRAT® | 50 |
| PHENYLACETALDEHYDE DIMETHYLACETAL | 1 |
| PYROPRUNATE | 2 |
| ROSE OXIDE | 1 |
| SANDRANOL® | 20 |
| UNDECAVERTOL | 5 |
| VERTOCITRAL | 1 |
| YSAMBER® K | 5 |
| Mixture 1 | 60 |

The perfume oil gives the washing powder the typical smell that one expects from this product. It transmits the message of cleanliness and freshness. In this case, the fragrance starts with a combination of aldehydes and citrus that reflect the freshness. Followed by the floral heart, which is the caring character. The base note consists of long-lasting components that have a woody, amber and musky character to give the impression of fresh laundry even after days.

Shampoo

| AGRUMEX HC | 80 |
|---|---|
| ALDEHYDE C14 SOG | 50 |

| | |
|---|---|
| ALDEHYDE C16 SOG. | 1 |
| AMBROXIDE | 4 |
| ANISALDEHYDE CLEAN | 16 |
| APPLE GREEN AROMABASE | 15 |
| APRIFLOREN ® | 1 |
| BERGAMOT OIL AUTHENTIC | 20 |
| CITRONELLOL 950 | 40 |
| CITRONELLYLACETATE EXTRA | 10 |
| DECALACTON GAMMA | 5 |
| DIHYDROMYRCENOL | 100 |
| DIPROPYLENGLYCOL | 8 |
| ETHYLVANILLIN 10% DPG | 4 |
| EUGENOL NAT. | 3 |
| FRAMBINON ® 10% DPG | 6 |
| GERANYLACETATE 60 | 20 |
| GERANYLTIGLINATE | 5 |
| GLOBALIDE ® | 25 |
| HEDION | 60 |
| HEXENAL TRANS-2 10% DPG | 6 |
| HEXENYLACETATE CIS-3 10% DPG | 9 |
| HEXYLACETATE | 50 |
| HEXYLSALICYLATE | 15 |
| INDOFLOR ® KRIST. 10% DPG | 2 |
| ISO E SUPER | 20 |
| ISORALDEIN 70 | 15 |
| JASMIN 61 TYPE BASE | 20 |
| LINALOOL | 60 |
| LINALYLACETATE | 150 |
| PHENIRAT ® | 50 |
| ROSE DE MAI-BASE | 30 |
| ROSE OXIDE L | 5 |
| SANDRANOL ® | 15 |
| VERTOCITRAL | 10 |
| Mixture 2 | 70 |

The perfume oil as a fragrance conveys the expectations one has of the product. In this case of a shampoo, you expect cleansing and care. This is conveyed by the fragrance. A clean apple/citrus combination reflects the cleansing part, while the heart of the fragrance (floral with fruity notes) is the caring aspect. The fragrance experience is rounded off by warm, woody and musky components.

The invention claimed is:

1. A mixture comprising: one or more stereoisomer(s) of a compound of formula (I)

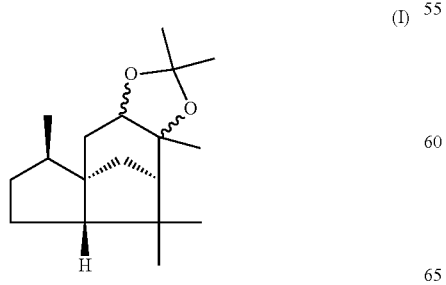

and two or more stereoisomers of a compound of formula (II)

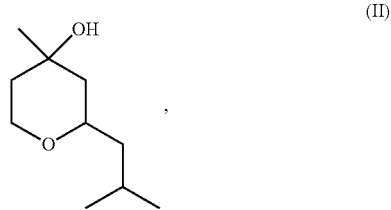

wherein a weight ratio of the total amount of compounds of the formula cis-(II)(+) and cis-(II)(−)

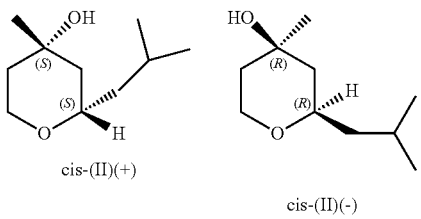

cis-(II)(+)                     cis-(II)(−)

to the total amount of compounds of the formula trans-(II)(+) and trans-(II)(−)

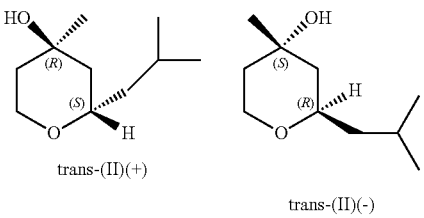

trans-(II)(+)                     trans-(II)(−)

is between 65:35 and 95:5.

2. The mixture according to claim 1, wherein the weight ratio of the total amount of stereoisomer(s) of the compound of the formula (I)

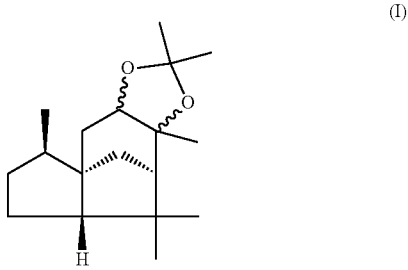

to the total amount of stereoisomers of the compound of formula (II)

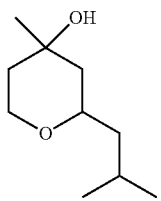
(II)

is between 1:12000 and 1:0.5.

3. The mixture of claim 2, wherein the total amount of stereoisomer(s) of the compound of formula (I) is sufficient to enhance the olfactory impression of the two or more stereoisomers of the compound of formula (II).

4. A mixture according to claim 1 obtained by a method comprising:

i) providing one or more stereoisomers of a compound of formula (I)

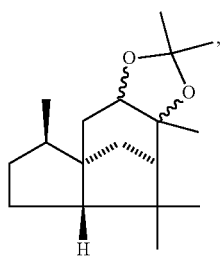
(I)

ii) providing two or more stereoisomers of a compound of formula (II)

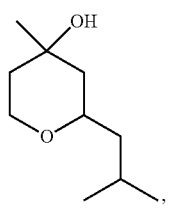
(II)

wherein a weight ratio of the total amount of compounds of the formula cis-(II)(+) and cis-(II)(−)

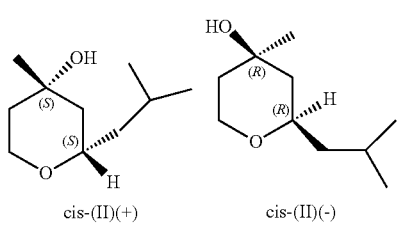

cis-(II)(+)         cis-(II)(−)

to the total amount of compounds of the formula trans-(II)(+) and trans-(II)(−)

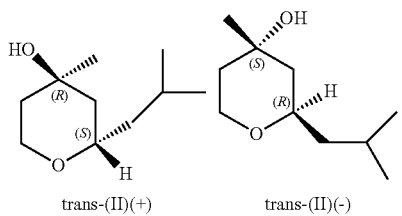

trans-(II)(+)         trans-(II)(−)

is between 65:35 and 95:5, and (iii) mixing the compounds provided in steps (i) and (ii).

5. The mixture of claim 1, wherein the weight ratio of the total amount of compounds of the formula cis-(II)(+) and cis-(II)(−) to the total amount of compounds of the formula trans-(II)(+) and trans-(II)(−) is between 75:25 and 85:15.

6. A mixture according to claim 1, wherein the weight ratio of the total amount of compounds of the formula cis-(II)(+) and cis-(II)(−) to the total amount of compounds of the formula trans-(II)(+) and trans-(II)(−) is between 65:35 and 90:10; and wherein the weight ratio of the total amount of the stereoisomer(s) of the compound of the formula (I) to the total amount of the stereoisomers of the compound of formula (II) is between 1:12000 and 1:0.5.

7. A method for modifying and/or enhancing the lily of the valley scent comprising:

i) providing one or more stereoisomer(s) of a compound of formula (I)

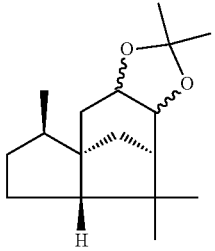
(I)

ii) providing two or more stereoisomers of a compound of formula (II)

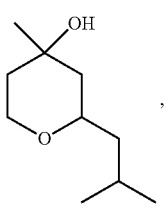
(II)

wherein a weight ratio of the total amount of compounds of the formula cis-(II)(+) and cis-(II)(−)

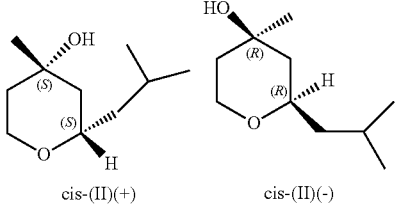

cis-(II)(+)   cis-(II)(−)

to the total amount of compounds of the formula trans-(II)(+) and trans-(II)(−)

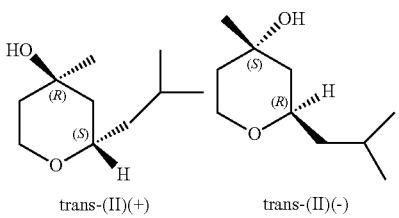

trans-(II)(+)   trans-(II)(−)

is between 65:35 and 95:5, and iii) mixing the compounds provided in steps i) and ii).

8. A fragrance composition comprising:

a mixture according to claim 1, and one or more additional fragrances selected from 3-(4-methyl-1-cyclohex-3-enyl)-butanal, 4-(4-hydroxyphenyl) butan-2-one, (E)-4-(2,6,6-trimethyl-1-cyclohex-2-enyl)but-3-en-2-one, (E)-4-(2,6,6-Trimethyl-1-cyclohex-2-enyl)but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]-but-3-en-2-one, 1-(2,6,6-Trimethyl-1-cyclohex-2-enyl)pent-1-en-3-one, [(Z)-Hex-3-enyl] methyl carbonate, 3-[(Z)-Hex-3-enoxy]propannitrile, 1-(2,3,8,8-tetramethyl-1,3,4,5,6,7-hexa-hydronaphthalen-2-yl)ethanone, spiro[1,3-dioxolane-2,5'-(4',4',8',8'-tetramethyl-hexahydro-3',9'-methanonaphthalene)], [3R-(3α,3a β,6β,7β,8aα)]-octa-hydro-6-methoxy-3,6,8,8-tetramethyl-1H-3a,7-methanoazulen, [3R-(3α,3aβ,7β,8aα)]-1-(2,3,4,7,8,8a-hexahydro-3,6,8,8-tetramethyl-1H-3a,7-methano-azulen-5-yl)ethan-1-one, 1-(2,2,6-trimethyl-cyclohexyl) hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl)acetate, (8E)-cyclohexadec-8-en-1-one, 1,3,4,6,7,8-hexahydro-4,6,6,7,8,8-hexamethyl-cyclopenta(g)-2-benzopyran, ethoxymethoxy-cyclododecane, 1,1,2,3,3-pentamethyl-2,5,6,7-tetrahydroinden-4-one, 1-(2,3,8,8-tetramethyl-1,3,4,5,6,7-hexa-hydronaphthalen-2-yl)ethanone.

9. The fragrance composition according to claim 8, wherein the total amount of stereoisomer(s) of the compound of formula (I)

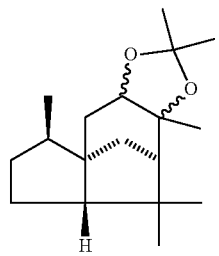

is sufficient to modify and/or enhance the olfactory impression of the two or more stereoisomers of the compound of formula (II)

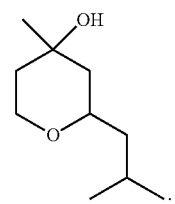

10. The fragrance composition according to claim 9, wherein the total amount of stereoisomer(s) of the compound of formula (I)

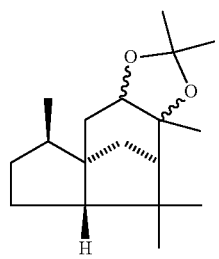

is 0.0001 to 10% by weight, based on the total weight of the fragrance composition.

11. The fragrance composition according to claim 10, wherein the total amount of stereoisomer(s) of the compound of formula (I) is 0.001 to 5% by weight, based on the total weight of the fragrance composition.

12. A product comprising a mixture according to claim 1 in a sensory effective amount, wherein the amount of the mixture, based on the total weight of the product, is in the range of 0.1 to 20% by weight.

13. The product of claim 12 being selected from perfume extraits, eau de parfums, eau de toilettes, shaving lotions, eau de colognes, pre-shave products, splash colognes, perfumed refreshing tissues, acidic, alkaline and neutral detergents, textile fresheners, ironing aids, liquid detergents, powdery detergents, laundry pre-treatments, fabric softeners, laundry soaps, washing tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

14. A fragrance composition comprising from 0.001 to 1 wt. % of a mixture according to claim 1.

15. A method for providing and/or enhancing a lily of the valley scent to a product, the method comprising:
(a) identifying a product to which a lily of the valley scent is to be provided and/or enhanced; and
(b) incorporating the mixture according to claim 1 into the product in an amount sufficient to provide and/or enhance the lily of the valley scent.

16. The method according to claim 7, further comprising verifying that the lily of the valley scent of the compounds of formula (II) has been modified and/or enhanced by the compounds of formula (I).

17. The method according to claim 7, wherein a weight ratio of the total amount of stereoisomer(s) of the compound of formula (I)

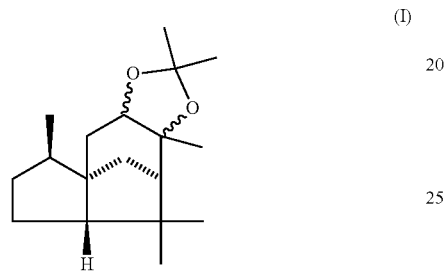

(I)

to the total amount of stereoisomers of the compound of formula (II)

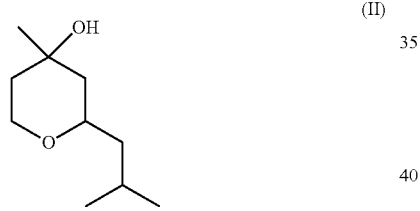

(II)

is between 1:12000 and 1:0.5.

18. The method of claim 7 further comprising:
(iv) providing one or more other components of a product to be manufactured; and
(v) contacting the other components provided in step (ii) with a sensory effective amount of the mixture of step (iii).

19. A mixture comprising:
one or more stereoisomer(s) of a compound of formula (I)

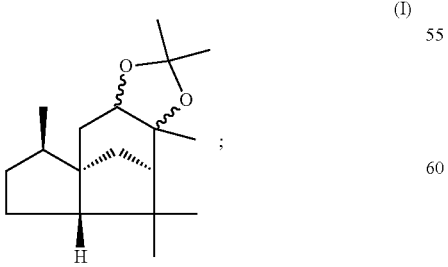

(I)

; and two or more stereoisomers of a compound of formula (II)

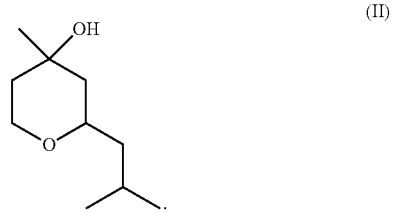

(II)

wherein a weight ratio of the total amount of compounds of the formula cis-(II)(+) and cis-(II)(−)

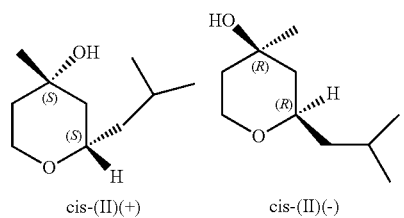

cis-(II)(+)   cis-(II)(-)

to the total amount of compounds of the formula trans-(II)(+) and trans-(II) (−)

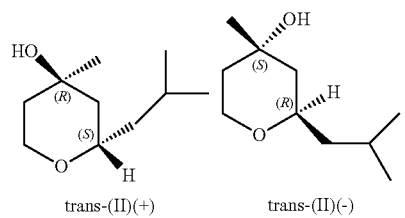

trans-(II)(+)   trans-(II)(-)

is between 65:35 and 95:5; and
wherein the mixture is free of additional fragrances other than the one or more steroisomer(s) of the compound of formula (I) and the two or more stereoisomers of a compound of formula (II).

20. The mixture according to claim 19 consisting of the one or more stereoisomer(s) of a compound of formula (I) and the two or more stereoisomers of a compound of formula (II).

* * * * *